United States Patent [19]

Sanvordeker

[11] 4,301,146
[45] Nov. 17, 1981

[54] STABILIZATION OF 16-OXYGENATED PROSTANOIC ACID DERIVATIVES

[75] Inventor: Dilip R. Sanvordeker, Elk Grove Village, Ill.

[73] Assignee: G. D. Searle & Co., Skokie, Ill.

[21] Appl. No.: 173,292

[22] Filed: Jul. 29, 1980

[51] Int. Cl.³ .................. A61K 31/74; A61K 31/215; A61K 31/19
[52] U.S. Cl. ...................................... 424/80; 424/305; 424/317; 424/362
[58] Field of Search .................. 424/80, 78, 362, 305, 424/317

[56] References Cited

U.S. PATENT DOCUMENTS

| | | | |
|---|---|---|---|
| 3,826,823 | 7/1974 | O'Rourke et al. | 424/80 |
| 3,965,143 | 6/1976 | Collins et al. | 424/305 |
| 4,058,623 | 11/1977 | Hoffmann et al. | 424/80 |
| 4,127,647 | 11/1978 | Sato et al. | 424/78 |

*Primary Examiner*—Sam Rosen
*Attorney, Agent, or Firm*—Albert Tockman; W. Dennis Drehkoff

[57] ABSTRACT

A stable solid dosage form of the compound ±methyl(7-[3(α)-hydroxy-2-β-(4(RS)-4-hydroxy-4-methyl-trans-1-octen-1-yl)-oxycyclopent-1α-yl]heptanoate, said solid dosage form comprising from about 50 to about 500 parts of a polymer selected from the group consisting of hydroxypropylmethyl cellulose and polyvinylpyrolidone per part of said compound.

22 Claims, No Drawings

STABILIZATION OF 16-OXYGENATED PROSTANOIC ACID DERIVATIVES

U.S. Pat. No. 3,965,143 discloses (±) methyl 7-[3(α)-hydroxy-2-β-(4(RS)-4-hydroxy-4-methyl-trans-1-octen-1-yl)-oxycyclopent-1α-yl[heptanoate, a potent anti-secretory agent. A related anti-secretary agent, (+) methyl-7-[3(α)-hydroxy-2-β-(4-(RS)-4-hydroxy-4-methyl-trans-1-octen-1-yl)oxycylopent-1-yl]-1-hept-4-cis-enoate is disclosed in commonly assigned, copending U.S. Patent Application U.S. Ser. No. 06/098,290 filed Nov. 28, 1979.

While the above compounds are potent anti-secretory agents, they are difficult to formulate because of their physical state as viscous liquids and their instability. The present invention provides stabilized compositions of the above anti-secretory agents.

The compounds are prostaglandin E-type compounds. Stabilization of prostaglandin E's is known in the art. See Derwent Abstract Nos. 90387A; 90386A; 90385A: 06805B and 32802W. Stabilization of the instant compounds has not previously been reported.

SUMMARY

The present invention provides improved compositions of two antisecretory agents: ±methyl(7-[3(α)-hydroxy-2-β-(4(RS)-4-hydroxy-4-methyl-trans-1-octen-1-yl)-oxycyclopent-1α-yl]]heptanoate(I) and ±methyl(7-[3(α)-hydroxy-2-β-(4-(RS)-4-hydroxy-4-methyl-trans-1-octen-1-yl)oxycyclopenta-1α-yl]-1-α-hept-4-cis-enoate(II). The compositions comprise a stabilized solid dispersion of a therapeutically effective amount of Compound I or II in a suitable polymer either alone or with fillers such as microcrystalline cellulose, mannitol and lactose.

The compounds are represented by Formulae I and II, respectively:

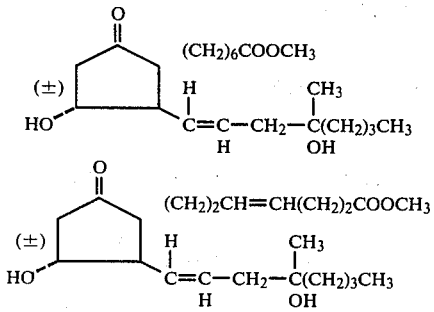

The compositions are generally prepared using a solvent stripping method.

DETAILED DESCRIPTION OF PREFERRED EMBODIMENTS

The improved compositions of this invention are solid dosage forms of Compounds 1 and 2 comprising drug and hydroxypropylmethyl cellulose or polyvinylpyrrolidone in ratios of from about 50 to about 500 parts of said polymer per part of drug.

The solid dispersions of the present invention are prepared by; (1) dissolving the anti-secretory agent (Compound 1 or 2) in an appropriate volume of a suitable solvent; (2) dissolving a polymer selected from the group consisting of hydroxypropylmethyl cellulose or polyvinylpyrrolidone in an appropriate volume of a suitable solvent; (3) adding the drug solution to the polymer solution; (4) stirring for from about 1 to 5 hours, preferably for about 2 to 4 hours at room temperature; (5) adding, if desired, up to 1000 parts of a filler selected from the group consisting of microcrystalline cellulose, mannitol and lactose; (6) flash evaporating the solvent; (7) blow-drying the residue under a nitrogen atmosphere and thereafter drying the solid dispersion in vacuo, at temperatures of from about 30° to 60° C., preferably from about 2 to 4 hours; subsequently grinding and sieving the solid dispersion; and thereafter storing at temperatures of from about +5° C. to 30° C., preferably from about 7° C. to 25° C. prior to use.

The solid dispersions of the present invention can be filled in capsules with or without additional excipients, or can be compressed into tablets in the usual manner.

Suitable solvents for Compounds I and II include, but are not limited to ethanol 200 proof, ethanol 3A grade, ethanol U.S.P. and dichloromethane, A.R. grade. The preferred solvent is dichloromethane and ethanol 3A grade.

Suitable solvents for the polymer include ethanol 200 proof, ethanol 3A grade, ethanol U.S.P. and dichloromethane, A.R. grade. The preferred solvent is ethanol 3A grade.

The following examples further illustrate the present invention.

EXAMPLE 1

Preparation of Stabilized Solid Dispersion of (±) methyl 7-[3(α)-hydroxy-2-β-(4(RS)-4-hydroxy-4-methyl-trans-1-octen-1-yl)oxocyclopent-1α-yl]]heptanoate (Compound 1) and hydroxypropylmethyl cellulose (1:500 ratio)

Compound 1 (210 mg) was dissolved in 180 ml of dichloromethane and added to a solution of hydroxypropylmethyl cellulose (HPMC) (100 g) in 1000 ml of dichloromethane. The combined solutions were stirred for 1 hour at room temperature, after which the solvent was flash evaporated and the residue dried under nitrogen gas and then in vacuo for 2 hours at 35° C. The dispersion was then ground, sieved through a 40 mesh screen and stored.

EXAMPLE 2

Following the method of Example 1, a solid dispersion of Compound 1 and hydroxypropylmethyl cellulose in a 1:100 ratio was prepared from 1560 mg of Compound 1 and 150 g of hydroxypropylmethyl cellulose. Compound 1 was dissolved in 200 ml of absolute ethanol. Hydroxypropylmethyl cellulose was dissolved in 0.9 L of absolute ethanol. The two were mixed and processed as described earlier.

EXAMPLE 3

A solid dispersion of Compound 1 and hydroxypropylmethyl cellulose, 1:50 ratio to 1:150 was prepared from 100–200 mg of Compound 1 and 10–15 g of hydroxypropylmethyl cellulose, using dichloromethane.

EXAMPLE 4

A solid dispersion of Compound 1, hydroxypropylmethyl cellulose and mannitol 1:250: 749 was prepared following the method of Example 1 from 400 mg of Compound 1, 100 g of hydroxypropylmethyl cellulose and 299.6 g of mannitol, adding the mannitol after mixing solution of Compound I in 100 ml and hydroxypropylmethyl cellulose in 2 liters of dichloromethane.

EXAMPLE 5

A solid dispersion containing 20 mg of Compound 1, 5 g of hydroxypropylmethyl cellulose and 14.98 g of Avicel PH101 microcrystalline cellulose (1:250: 749) was prepared by the method of Example 4, using dichloromethane (300 ml) as the solvent.

EXAMPLE 6

A solid dispersion containing 20 mg of Compound 1, 5 g of hydroxypropylmethyl cellulose and 14.98 g of mannitol (1:250: 749) was prepared by the method of Example 4 using dichloromethane as the solvent.

EXAMPLE 7

The stability the solid dispersions of Example 1, 2 and 3 was determined at 5° C., 40° C. over a 12–26 week period by incubating samples. The results are summarized in Table I (Example 1), Table II (Example 2) and Table III (Example 3) for a predetermined period at each temperature and thereafter assaying the samples by high pressure liquid chromatography for Compound 1. All analysis was done using a Waters Associate Liquid Chromatograph equipped with Model 6000A Pump, V6K Injector and Model 450 Variable Wavelength Detector set at VV, 205 mm at 1.10AUFS and a chart speed of 1 cm 1 min. Analysis was achieved utilizing a Partisil 10/25 ODS 25 cm×4.6 mm ID column (Whatman, Incorporated), eluted with acetonitrile at a flow rate of 2.0 ml/minute.

TABLE 1

Stability Data on Compound 1 alone and its HPMC Dispersion

A. Compound 1 alone (Unstabilized)

% Potency (Extraction + HPLC Assay)*

| Storage Period | | Time in Weeks | | | | | | | |
|---|---|---|---|---|---|---|---|---|---|
| | | 0 | 1 | 2 | 3 | 4 | 6 | 8 | 12 | 14 |
| Storage Temperatures | 55° C. | — | 72.7 | 44.0 | 26.6 | 27.8 | — | — | — | — |
| | 40° C. | — | — | — | — | 87.0 | — | 55.0 | 41.55 | |
| | 30° C. | — | — | — | — | — | 79.6 | — | 75.3 | — |
| | 5°–7° C. (2 wks) | 94.8 | — | — | — | — | — | — | 93.1 | 86.1 |

B. Compound 1 HPMC Dispersion

% Potency (Extraction + HPLC Assay)*

| Storage Period | | Time in Weeks | | | | | | | |
|---|---|---|---|---|---|---|---|---|---|
| | | 0 | 1 | 2 | 3 | 4 | 6 | 8 | 12 | 14 |
| Storage Temperature | 55° C. | — | 90.9 | 89.9 | 89.1 | 96.7 | 88.5 | 92.8 | — | — |
| | 40° C. | — | — | — | — | 97.0 | — | 92.6 | 83.1 | 88.3 |
| | 30° C. | — | — | — | — | — | 87.7 | — | 89.9 | 87.2 |
| | 5°–7° C. (2 wks) | 94.4 | — | — | — | — | — | — | 82.5 | 87.2 |

*Average of duplicate assays/point.

TABLE 2

A. Solid State Stability of Compound 1: HPMC (1:100) Dispersion Prepared with Ethanol and Dichloromethane % SC-29333 Remaining Time (Weeks)

| Condition | 0 | 1 | 2 | 3 | 4 | 6 | 8 | 12 | 26 |
|---|---|---|---|---|---|---|---|---|---|
| 70° C. | 100 | 91.92 | 89.47 | 86.70 | 90.07 | | | | |
| 55° C. | 100 | — | 94.74 | 93.26 | 97.32 | | 95.10 | 92.80 | |
| 40° C. | 100 | — | — | 94.92 | — | 92.70 | — | 97.09 | 102.9 |
| 30° C. | 100 | — | — | — | 99.63 | | 91.41 | 98.52 | 104.7 |
| 5° C. | 100 | — | — | — | | | 102.21 | 100.46 | 107.4 |

B. Solid Stability of Compound 1: HPMC (1:100) Dispersion Prepared with Methylene Chloride % SC-29333 Remaining Time (Weeks)

| Condition | 0 | 1 | 2 | 3 | 4 | 6 | 8 | 12 | 34 |
|---|---|---|---|---|---|---|---|---|---|
| 70° C. | 100 | 97.27 | 85.36 | — | 87.74 | | | | |
| 55° C. | 100 | — | 97.28 | — | — | 93.43 | — | 90.47 | |
| 30° C. | 100 | — | — | — | — | — | 106.08 | — | 103.6 |
| +5° C. | — | — | — | — | — | — | 98.0 | 102.53 | 105.1 |

TABLE III

Solid State Stability of Compound 1: HPMC Dispersions (Comparision of Compound 1: HPMC Ratios 1:50, 1:100, 1:150)
% Compound 1 Remaining (Initial Assay as 100%)

| TIME (Weeks) | 70° C. RATIO | | | 55° C. RATIO | | | 30° C. RATIO | | | +5° C. RATIO | | |
|---|---|---|---|---|---|---|---|---|---|---|---|---|
| | 1:50 | 1:100 | 1:150 | 1:50 | 1:100 | 1:150 | 1:50 | 1:100 | 1:150 | 1:50 | 1:100 | 1:150 |
| 1 | 103.40 | 87.25 | 92.50 | — | — | — | — | — | — | — | — | — |
| 2 | 85.97 | 85.36 | 80.48 | 98.52 | 97.28 | 97.28 | — | — | — | — | — | — |
| 4 | 90.86 | 87.74 | 72.79 | — | — | — | 112.35 | 108.56 | 103.2 | — | — | — |
| 6 | | | | 96.38 | 93.43 | 92.45 | — | — | — | — | — | — |
| 8 | | | | 97.84 | — | 91.49 | 106.25 | 106.08 | 100 | 107.68 | 98.0 | 96.50 |
| 12 | | | | 98.69 | 90.47 | 81.77 | | | | 108.03 | 102.53 | 103.13 |

EXAMPLE 8

The stability of the solid dispersions of Example 4, 5 and 6 were determined under various conditions. The results (% of Compound 1 extracted) are set forth in TABLE IV.

TABLE IV

Effect of Excipients on Stability of Compound 1: HPMC Solid Dispersions

| Example No. | Temperature | Period | % Compound 1 Extracted (HPLC Assay) |
|---|---|---|---|
| 1 | R.T. | initial | 94.8 (100%) |
| | 40° C. | 18 weeks | 90.17 (96.16%) |
| 4 | R.T. | initial | 11.15 (100%) |
| | 55° C. | 4 weeks | 110.5 (100%) |
| | 55° C. | 4 weeks | 106.1 (95.45%) |
| 5 | R.T. | initial | 110.7 (100%) |
| | 55° C. | 4 weeks | 109.3 (101.2%) |
| | 55° C. | 8 weeks | 112.3 (101.4%) |
| 6 | R.T. | initial | 104.1 (100%) |
| | 55° C. | 2 weeks | 91.8 (88.18%) |
| | 55° C. | 6 weeks | 98.5 (94.62%) |
| | 55° C. | 8 weeks | 95.7 (91.93%) |
| | 55° C. | 12 weeks | 88.6 (85.11%) |
| | 55° C. | 17 weeks | 84.9 (81.55%) |
| | 70° C. | 1 week | 105.3 (101.1%) |
| | 70° C. | 2 weeks | 94.6 (90.8%) |
| | 70° C. | 3 weeks | 85.55 (82.18%) |
| | 70° C. | 4 weeks | 73.10 (70.22%) |
| | 70° C. | 6 weeks | 76.65 (73.63%) |

EXAMPLE 9

Preparation of Filled Capsules 1.5 Grams of a solid dispersion of ±methyl(7-[3(α)-hydroxy-2-β-(4RS)-4-hydroxy-4-methyl-trans-1-octen-1-yl)-oxocyclopent-1α-yl]heptanoate and polyvinylpyrrolidone, containing 200 μg of drug per 100 mg of dispersion, were blended with 7.5 g of lactose (DTG.U.S.P. grade powder). The mixture was placed on a ball mill for 10 minutes. Thereafter, Number 2 gelatin capsules were filled with an average of about 296 mg of the blended mixture. Each capsule thus contained approximately 100 μg of drug.

EXAMPLE 10

Preparation of Filled Capsules

To 4.8 grams of a solid dispersion of ±methyl(7-[3(α)-hydroxy-2β-4(RS)-4-hydroxy-4-methyl-trans-1-octen-1-yl)oxycyclopent-1-yl]-1-hept-4-cis-enoate and hydroxypropylmethyl cellulose, containing 200 μg of drug per 100 mg of dispersion, was added 24.8 g of anhydrous DTG lactose. The powders were mixed intimately for 10 minutes with a mortor and pestle, and sifted three times through a 30 mesh screen. Thereafter, No. 2 gelatin capsules were filled with 314 mg of the blended mixture. Each capsule contained 106.9 μg of drug.

EXAMPLE 11

Preparation of Tablets 25,000 Tablets each containing 200 mcg of ±methyl (7-[3(α)-hydroxy-2-β-(4RS)-4-hydroxy-4-methyl-trans-1-octen-1-yl)-oxycyclopent-1-yl]heptanoate were prepared using a 1:100 solid dispersion of drug and hydroxy propyl methyl cellulose with the following ingredients:

| Ingredient | Amount per batch(g) | Amount per dose (mg) |
|---|---|---|
| Solid Dispersion | 511.75 | 20.47 |
| Microcrystalline cellulose, N.F. (Avicel PH103, FMC Corp) | 4388.25 | 175.53 |
| Sodium glycolate starch, U.S.P. | 75.0 | 3.0 |
| Hydrogenated castor oil | 25.0 | 1.0 |
| | 200.00 mg | 5,000.00 g |

Tablets of varying dosages of drug can be prepared so long as the dosage per tablet or per dose administered is within the range of from about 50 to about 200 mcg per dose.

I claim:

1. A stable solid dispersion of the compound ±methyl(7-[3(α)-hydroxy-2-β-(4RS)-4-hydroxy-4-methyl-trans-1-octen-1-yl)-oxycyclopent-1α-yl]heptanoate, said solid dispersion comprising from about 50 to about 500 parts of a polymer selected from the group consisting of hydroxypropylmethyl cellulose and polyvinylpyrolidone per part of said compound.

2. A dispersion of claim 1 additionally comprising a filler selected from the group consisting of microcrystalline cellulose, mannitol and lactose.

3. A dispersion of claim 2 wherein up to 1000 parts of filler per part of drug is employed.

4. A solid dispersion of claim 1 wherein said polymer is hydroxypropylmethyl cellulose.

5. A solid dispersion of claim 2 or 4 wherein said polymer is hydroxypropylmethyl cellulose and said filler is microcrystalline cellulose.

6. a solid dispersion of claim 2 or 4 wherein said polymer is hydroxypropylmethyl cellulose and said filler is mannitol.

7. A solid dosage form of claim 1 or 2 wherein said polymer is polyvinylpyrrolidone.

8. A solid dispersion of claim 2 or 4 wherein said polymer is polyvinylpropylene and said filler is microcrystalline cellulose.

9. A solid dispersion of claim 2 or 4 wherein said polymer is polyvinylpyrrolidone and said filler is mannitol.

10. A stable solid dosage form of the compound ±methyl-(7-[3(α)-hydroxy-2β-(4(RS)-4-hydroxy-4-methyl-trans-1-octen-1-yl)oxycyclopent-1α-yl]hept-4-cis-enoate, said solid dosage form comprising from about 50 to about 500 parts of a polymer selected from the group consisting of hydroxypropylmethyl cellulose and polyvinylpyrrolidone per part of said compound.

11. A dosage form of claim 10 additionally comprising a filler selected from the group consisting of microcrystalline cellulose, mannitol and lactose.

12. A dosage form of claim 11 wherein up to 1000 parts of filler per part of drug is employed.

13. A solid dosage form of claim 10 wherein said polymer is hydroxypropylmethyl cellulose.

14. A solid dosage form of claim 11 or 13 wherein said polymer is hydroxypropylmethyl cellulose and said filler is microcrystalline cellulose.

15. A solid dosage form of claim 11 or 13 wherein said polymer is hydroxypropylmethyl cellulose and said filler is mannitol.

16. A solid dosage form of claim 10 or 11 wherein said polymer is polyvinylpyrrolidone.

17. A solid dosage form of claim 11 or 13 or wherein said polymer is polyvinylpyrrolidone and said filler is microcrystalline cellulose.

18. A solid dosage form of claim 11 or 13 wherein said polymer is polyvinylpyrrolidone and said filler is mannitol.

19. A solid dosage form of claim 11 or 13 wherein said polymer is polyvinylpyrrolidone and said filler is lactose.

20. A solid dosage form of claim 11 or 13 wherein said polymer is hydroxypropylmethyl cellulose and said filler is lactose.

21. A solid dosage form of claim 2 or 4 wherein said polymer is hydroxypropylmethyl cellulose and said filler is lactose.

22. A solid dosage form of claim 2 or 4 wherein said polymer is polyvinylpyrrolidine and said filler is lactose.

* * * * *